United States Patent [19]

Taylor et al.

[11] Patent Number: 4,551,553
[45] Date of Patent: * Nov. 5, 1985

[54] DECOMPOSITION OF HYDROPEROXIDES IN THE PRESENCE OF HOMOGENEOUS BINARY CATALYSTS

[75] Inventors: Paul D. Taylor, Berwyn; Michael T. Mocella, West Chester, both of Pa.

[73] Assignee: Atlantic Richfield Company, Los Angeles, Calif.

[*] Notice: The portion of the term of this patent subsequent to Apr. 2, 2005 has been disclaimed.

[21] Appl. No.: 468,261

[22] Filed: Feb. 22, 1983

[51] Int. Cl.[4] .................... C07C 45/53; C07C 37/08
[52] U.S. Cl. .................................. 568/311; 568/342; 568/385; 568/798; 568/840; 568/835; 568/816; 568/306; 568/815
[58] Field of Search ............... 568/311, 342, 385, 798, 568/840, 835, 816, 306, 815

[56] References Cited

U.S. PATENT DOCUMENTS

| | | | |
|---|---|---|---|
| 3,879,467 | 4/1975 | Zajacek et al. | 568/342 |
| 3,925,316 | 12/1975 | Brunie et al. | 568/342 |
| 3,927,105 | 12/1975 | Brunie et al. | 568/342 |
| 3,928,452 | 12/1975 | Brunie et al. | 568/311 |
| 3,941,845 | 3/1976 | Voskuil et al. | 568/342 |
| 4,042,630 | 8/1977 | Wolters et al. | 568/342 |

*Primary Examiner*—James H. Reamer
*Attorney, Agent, or Firm*—Michael S. Jarosz

[57] ABSTRACT

The process of decomposing a hydroperoxide by contacting the hydroperoxide with a catalytic quantity of a catalyst system comprised of chromium and ruthenium. The catalyst system is characterized by its high stability while exhibiting improved activity for hydroperoxide decomposition and selectivity to desired alcohol and ketone products.

16 Claims, No Drawings

DECOMPOSITION OF HYDROPEROXIDES IN THE PRESENCE OF HOMOGENEOUS BINARY CATALYSTS

BACKGROUND OF THE INVENTION

1. Field of the Invention

This invention relates to a process for decomposing hydroperoxides at elevated temperatures in the presence of a specific binary homogeneous catalyst comprised of chromium and ruthenium which is stable and exhibits improved activity, as well as selectivity for organic hydroperoxide decomposition to the desired alcohol and ketone products.

2. Description of the Prior Art

The decomposition of hydroperoxides catalyzed by transition metal complexes has been investigated for a number of years. It is generally assumed that in the first stage of decomposition, the hydroperoxide molecule forms an active complex with the metal catalyst. This complex decomposes subsequently into free radicals or molecular species which yield final products in further reactions.

In U.S. Pat. No. 3,879,467 there is disclosed a process for the catalytic oxidation of certain hydrocarbons utilizing an organic hydroperoxide in the presence of a chromium catalyst to produce alcohols and ketones as the primary products. Also disclosed in this patent for this purpose are a number of other specific metal catalysts which resulted in low hydroperoxide conversions or low product yields, or both, or in instances where high conversions were noted, almost no product yields were obtained.

In U.S. Pat. No. 3,925,316, a process is disclosed for the preparation of mixtures of cycloalkanols and cycloalkyl ketones by heating cycloalkyl hydroperoxides in the presence of, as catalyst, a soluble derivative of vanadium, molybdenum, or ruthenium.

Certain forms of ruthenium have also been reported in recent publications in connection with cumene hydroperoxide decomposition studies. In this regard, attention is directed to "Use of the Proton NMR Relaxation Method to Study the Coordination of Cumene Hydroperoxide With Cobalt and Ruthenium Carboxylates", V. M. Nekipelov, Dokl. Akad. Nauk SSSR, V 261 (6), 1377–81 (1981); "NMR Studies of .Mu3-Oxotriruthenium Hexacarboxylate Cumene Hydroperoxide Interaction", A. M. Trzeciak, Oxid. Commun., V. 1 (4), p. 295–303 (1980); and "Cumene Hydroperoxide Decomposition Reaction Catalyzed by Ruthenium (III) beta.-diketonates", A. M. Trzeciak, et al, React. Kinet. Catal. Lett., V. 12 (1–2), p. 121–5 (1981); and "Decomposition of Organic Hydroperoxides on Ruthenium .pi.-Complexes", Yu A. Aleksandrov, Ah. Obshch. Khim., V. 48 (9), p. 2142 (1978).

Binary homogeneous metal catalyst combinations previously disclosed for decomposition of specific hydroperoxides include the combination of a particular salt of iron and copper in U.S. Pat. No. 3,401,193, and an admixture comprised of cobalt and chromium compounds for effecting cyclohexane oxidation and decomposition of resultant hydroperoxide in U.S. Pat. No. 3,987,100.

The use of heterogeneous metal catalysts has also been disclosed in recently issued publications, for example, in U.S. Pat. No. 4,173,587, there is disclosed the use of a non-soluble rhenium compound for the decomposition of cumene hydroperoxide; in U.S. Pat. No. 4,209,465, there is disclosed the decomposition of cumene hydroperoxide by use of specified carbonium, tropylium or oxonium salts as catalysts; and in U.S. Pat. No. 4,059,598, there is disclosed the decomposition of residual hydroperoxides resulting from propylene epoxidation in the presence of a homogeneous cobalt oxide catalyst which may also contain copper oxide as a promoter.

However, prior art catalyst systems were deemed unsatisfactory in their ability to provide a stable catalyst system or lacked desired activity in the decomposition of hydroperoxide, or failed to provide the selectivity to the desired product(s). In an effort to correct one or more of these apparent deficiencies, the trend has been to employ stabilizing ligands in combination with certain metallic catalysts; however, many of these ligands are not readily available and are expensive to employ in any large quantity, especially on a commercial scale.

SUMMARY OF THE INVENTION

It has now been discovered that hydroperoxides may be decomposed by use of a catalytically significant quantity of a binary homogeneous catalyst system comprising an admixture of ruthenium and chromium, thereby eliminating the need for expensive and difficult to obtain stabilizing ligands. The catalyst system employed in the process of the present invention is characterized by its stability over extended periods of time in use while exhibiting improved activity for organic hydroperoxide decomposition and selectivity to the desired alcohol and ketone products in the case of organic hydroperoxide decomposition. Thus, the present invention comprises a process for the catalytic decomposition of a wide variety of hydroperoxides in high yield and selectivity to the desired products by employing a stable binary homogeneous catalyst system comprised of ruthenium and chromium in particular proportions.

DETAILED DESCRIPTION OF THE INVENTION

Although any hydroperoxide is deemed capable of decomposition in accordance with the process of the present invention, in general, typical hydroperoxides employable conform to the general formula:

$$R\text{---}OOH$$

wherein R is a member selected from the group consisting of hydrogen, a straight or branched chain alkyl or cycloalkyl group containing of from 2 to 15 carbon atoms, an aryl group such as a monocyclic or polycyclic group in which the cyclic groups may optionally be substituted with one or more substituents inert to the decomposition reaction, such as alkyl or alkoxy containing of from 1 to 7 carbon atoms, nitro, carboxyl or carboxyl ester containing up to about 15 carbon atoms and a halogen atom such as chloride, brinude, or an alkaryl group in which the alkyl chain contains from 1 to 15 carbon atoms and the aryl group is as above described. Preferably, R is hydrogen, an alkyl or cycloalkyl group containing of from 4 to 12 carbon atoms or an alkaryl group in which the aromatic moiety is phenyl and the alkyl substituent is straight or branched chain alkyl or cycloalkyl containing up to about 6 carbon atoms. Illustrative preferred organic hydroperoxides employed as starting materials in the process of the present invention include tertiary butyl and isobutyl hydroperoxide, 2-methylbutyl-2 hydroperoxide, cyclohexyl hydroperoxide, α- and β-ethylbenzene hydroperoxide, cumene hydroperoxide, cyclohexylphenyl hydroperoxide and hydrogen peroxide.

The decomposition of the hydroperoxide in the presence of the binary homogeneous catalyst system of the present invention is carried out in known manner. In general, the reaction proceeds very rapidly over a wide variety of reaction conditions. Reaction temperatures employed may range from about 25° C. to about 250° C., and preferably between 50° C. and 150° C. In order to avoid the production of undesired by-products, the reaction temperature is not permitted to attain too high a level, thereby precluding thermal decomposition of the hydroperoxide. In addition, the products obtained by the process of the present invention, other than the desired primary alcohol and ketone products, in the case of decomposition of an organic hydroperoxide, illustratively aldehydes, acids and peroxides, are removed during the decomposition reaction in order to reduce the possibility of undesired side reactions. Pressure at which decomposition is carried out is not critical and removal of such by-products may be effected by conducting the decomposition under reduced pressure. In general, atmospheric and super-atmospheric pressure up to 150 atmospheres, i.e. pressures sufficient to maintain the reactants in the liquid phase, may be conventionally employed.

The reaction time required for effecting completion of the decomposition of the hydroperoxide will depend on catalyst and hydroperoxide concentration and temperature. In general, decomposition of the organic hydroperoxide will be substantially completely effected in batch operation within 0.1 to 1000 minutes, preferably 1 to 60 minutes. In continuous operation, any convenient conversion rate may be adapted, depending upon catalyst concentration and proportions, nature of diluent, if employed, and consumption of liberated oxygen from hydroperoxide decomposition.

If desired, in order to more readily facilitate carrying out of the reaction, e.g. for recycle of the catalyst contained therein, the process of the present invention may be carried out in the presence of a diluent or solvent. Typical diluents employable in the process of the present invention are hydrocarbons from which the organic hydroperoxides may have been derived by oxidation, i.e. precursor starting materials, such as cyclohexane in the case where the desired hydroperoxide is cyclohexyl hydroperoxide, reaction by-products, such as acids and esters obtained in the reaction, or the alcohol which is the product of the reaction of the decomposition, for example, tertiary butyl alcohol in the case of the decomposition of tertiary butyl hydroperoxide. In the event the diluent employed is reactive under the reaction conditions of the process, either with the hydroperoxide or with liberated molecular oxygen, increased yields of the desired alcohol or ketone products are obtainable. If employed, the diluent is generally present in an amount between about 10 and 98 percent, by weight, and preferably between about 50 and 97 percent, by weight, based on the total weight of the reaction mixture. When such a diluent is employed, as will be appreciated by those skilled in the art, the reaction is effected at a rate and under reaction conditions of temperature and pressure sufficient to avoid excessive build-up of liberated oxygen, thereby precluding formation of a flammable composition in the vapor phase. Alternatively, if desired, the decomposition reaction may be carried out in the presence of an inert gas such as nitrogen or argon to dilute non-condensible gaseous products, primarily liberted oxygen, to avoid formation of a flammable gaseous mixture.

The binary homogeneous catalyst system of the present invention comprises an admixture of ruthenium and chromium compounds which are soluble in the liquid hydroperoxide to be decomposed or in the aforementioned diluent. Representative examples of ruthenium and chromium compounds employable in the process of the invention include ruthenium and chromium salts of carboxylic acids, salts of organic acids produced in the course of oxidation of the precursor hydrocarbon from which the organic hydroperoxide may have been obtained, carbonyls, sulfates, nitrates, halides, and organometalic compounds of those metals. Representative examples of ruthenium compounds include ruthenium naphthenate, ruthenium octoate, ruthenium laurate, ruthenium stearate, ruthenium linoleate, ruthenium acetylacetonate ruthenium nitrate, ruthenium chloride, ruthenium sulfate and ruthenium carbonyl. Representative examples of chromium compounds include chromium naphthenate, chromium octoate, chromium laurate, chromium palmatate, chromium stearate, chromium linoleate, chromium acetylacetonate, chromium nitrate, chromium chloride, chromium sulfate and chromium carbonyl. Representative examples of organic acids which may be produced in the course of oxidation of the hydrocarbon starting material precursor to the organic hydroperoxide include: acetic, formic, propionic, isobutyric, caproic, valeric, adipic, glutaric, hydroxycaproic and benzoic acids.

As indicated, it was unexpectedly found in accordance with the process of the present invention, that a stable homogeneous catalyst suitable for effecting decomposition of the hydroperoxide specified at high activity and selectivity to desired alcohols and ketones may be obtained by employing a relatively inexpensive promoting chromium-containing compound, together with an active ruthenium compound, without necessity of employment of expensive and difficult to obtain stabilizing ligands. The concentration of the catalyst in the liquid phase may vary widely. In general, the binary homogeneous catalyst system of the present invention may advantageously be employed in amounts ranging from about 0.01 ppm to about 5,000 ppm of ruthenium and from about 0.01 to about 5,000 ppm of chromium, preferably 0.1 to 1,000 ppm of ruthenium and 0.1 to 1,000 ppm of chromium, each as metals. The upper limit of catalyst concentration appears to be dictated and controlled, however, more by economics in view of the relatively higher cost of ruthenium, and no particular advantages at the higher concentration stated are manifest. Since it is preferred to use lower quantities of catalyst in view of the cost of ruthenium metal, the stability of the catalyst system enhances the operating economics. Although these metals may be employed on an equal weight basis, in general, the proportion of chromium to ruthenium will range from about 0.5:1 to 10:1, and higher, in achieving the objectives of the process. In addition, it has been found, in accordance with the present invention, that a hydroperoxide concentration of at least 1%, and preferably of at least 3%, should be maintained during the decomposition reaction to maintain catalyst stability, i.e., preclude precipitation of at least a portion of the metal catalyst. If desired, the catalyst may also be employed in fixed-bed operation in known manner on a conventional carrier or in conjunction with a polymer support such as a polyvinylpyridine, polypyrrolidone or polyphthalocyanine. Further, if desired, the catalyst system may optionally be employed with a ligand, although such operation is not required as above indicated.

The invention is further illustrated by the following examples in which all temperatures are in degrees Centigrade and all percentages are by weight unless otherwise specified.

EXAMPLE I-VI

To a 100 ml. flask equipped with a condenser and a side arm capped with a rubber septum for liquid sampling, there is charged 100 ppm of the metal or mixture of metals as their salts identified in Table I, below, solubized in 40 cc of an oxidation reaction product (Reactant Feed) obtained from the non-catalyzed molecular oxygen oxidation of isobutane containing 42 parts of tertiary butyl hydroperoxide (TBHP), 56 parts of tertiary butyl alcohol (TBA) and 2 parts of a crude mixture comprised of low molecular weight oxygen-containing liquids. The flask and contents are rapidly heated to reflux temperature, about 78° C., by immersing in an oil bath, and held at such temperature for a period of 2 hours. Liquid samples are withdrawn after the indicated period and analyzed by gas-liquid chromotagraphy. Table I sets forth the results of the decomposition reaction.

TABLE I

| Ex. No. | Metal Salt Catalyst | TBHP Decomposition wt (%) | Physical Characteristics of Reaction Product |
|---|---|---|---|
| I | Chromium (III) Acetylacetonate | 4.3 | clear, deep yellow solution |
| II | Cobalt (II) Acetylacetonate | 37.4 | turbid, pink solution containing precipitated metal |
| III | Manganese (II) Acetylacetonate | 16.9 | turbid, pinkish solution containing white precipitate |
| IV | Ruthenium (III) Acetylacetonate | 99.0 | turbid, green solution containing grey precipitate |
| V | Equimolar mixture of: Ruthenium (III) and Chromium (III) Acetylacetonates | 96.6 | clear yellow solution with no precipitate |
| VI | Equimolar mixture of: Cobalt (II) and Chromium (III) Acetylacetonates | 48.1 | clear yellow solution |

The results of the experiments set forth in Table I, above, demonstrate the superior activity of ruthenium for decomposition of tertiary butyl hydroperoxide and that equimolar admixtures of ruthenium and chromium provide a stable catalyst system for the decomposition of hydroperoxides while maintaining high activity for the decomposition reaction.

EXAMPLES VII-XI

The examples set forth below demonstrate continuous operation of the process of the invention.

The apparatus employed is a glass reactor having a volume of approximately 50 cc equipped with a stirrer, a side-arm used to feed the hydroperoxide containing solution, a glass thermocouple well and an additional side arm for removal of the alcohol product as a vapor. Nitrogen is fed at a rate of 85 cc per minute to the reactor through the inlet side arm to dilute the non-condensable product, primarily oxygen. The reactor is glass-jacketed and equipped with inlet and outlet arms to permit a continuous circulation of oil from a heating bath to maintain the reaction temperature at reflux temperature.

The reactor is charged with 10 grams of the Reactant Feed described in Example I above, having the catalyst or catalyst mixture indicated in Table II below, solubilized therein. Reactant Feed is metered continuously from a graduated reservoir over the period indicated. The vapor product from the reactor is cooled by passing over a condenser maintained at 25° C. The liquid condensate is analyzed by gas-liquid chromatography for tertiary butyl alcohol (TBA), acetone, methanol, ditertiary butyl peroxide (DTBP) and tertiary butyl hydroperoxide (TBHP). The non-condensible gases are monitored by gas chromotography for carbon dioxide, carbon monoxide, methane, oxygen and nitrogen. The results obtained are set forth in Table II, below:

TABLE II

| Example No. | Catalyst[1] (ppm) | Average Rate of TBHP Decomposition[2] | Time[3] | Product Selectivity (%) TBA/Methanol/DTBP/Acetone | | | | Physical Characteristics of Reaction Products |
|---|---|---|---|---|---|---|---|---|
| VII | Ruthenium III (100) | 31,700 | 6 | 83.6 | 2.7 | 3.8 | 9.9 | turbid solution containing grey precipitate |
| VIII | Ruthenium III (10) and Chromium III (10) | 89,900 | 6 | 90.4 | 1.1 | 4.7 | 3.8 | clear solution |
| IX | Ruthenium III (100) and Chromium III (50) | 7,900 | 16 | 91.6 | 0.8 | 4.4 | 3.2 | clear solution |
| X | Cobalt II (100) and Chromium III (100) | 5,300 | 5 | 92.2 | 0.5 | 4.6 | 2.7 | clear solution |
| XI | Ruthenium III (25) and Chromium III (25) | 43,875 | 116 | 86.1 | 2.9 | 4.2 | 6.8 | clear solution |

[1]present as the acetylacetonate salt in 10 grams of Reactant Feed
[2]grams of TBHP decomposed/gram of metal catalyst/hour
[3]hours of continous operation The results of the above experiments set forth in Table II demonstrate that ruthenium exhibits high activity for continuous hydroperoxide decomposition and that chromium exhibits a stabilizing effect over extended periods of time on ruthenium during the decomposition reaction while maintaining high activity and selectivity to desired tertiary butyl alcohol product.

EXAMPLE XII

Into a 300 cc stainless steel stirred reactor, there is charged 58 parts of isobutane and the reactor is heated to a temperature of 111° C. Thereafter, 100 parts of the Reactant Feed described in Example I above, is premixed with a binary catalyst comprised of 3 ppm of ruthenium III acetylacetonate and 3 ppm of chromium III acetylacetonate and the resultant admixture is added to the reactor under 1200 to 1300 psig nitrogen pressure. The reaction is conducted isothermically over a period of 2.5 hours at which point analysis of the reaction products is made by gas-liquid chromotography. The results indicate a tertiary butyl hydroperoxide conversion of 98%, with molar selectivities to: tertiary butyl alcohol of 85.6; acetone 7.5%; ditertiarybutyl peroxide of 5.5%; methyl ethyl ketone of 0.1%; and unidentified by-products of 1.3%. Incorporation of liberated molecular oxygen into the products of the reaction of 72.4% is obtained.

This Example demonstrates that a mixture of soluble ruthenium and chromium constitutes a very active and stable catalyst for decomposition of TBHP in the presence of isobutane. Under the operating conditions employed, the active oxygen of decomposed TBHP can be substantially consumed to produce products other than molecular oxygen, thereby significantly reducing costs associated with dilution and recycle or disposal of large quantities of liberated oxygen.

EXAMPLE XIII

The same procedure is followed as in Example I, except that ethyl benzene hydroperoxide and ethyl benzene are employed as the hydroperoxide and diluent, respectively, and a catalyst system comprised of 50 ppm of ruthenium and 50 ppm of chromium, each in the trivalent state and present as the acetylacetonate salt, is employed.

The results indicate that 97% of the hydroperoxide decomposes and quantitative analysis, by gas-liquid chromotography, of the resulting crude products shows a yield of α methylbenzyl alcohol and acetophenone of 92%, based on the hydroperoxide feed. The reaction product is a clear solution with no detectable quantities of any precipitate, indicating stability of the catalyst.

EXAMPLE XIV

The same procedure is followed as in Example I, except that cumene hydroperoxide and cumene are employed as the hydroperoxide and diluent, respectively, and a catalyst system comprised of 50 ppm of ruthenium and 50 ppm of chromium, each in the trivalent state and present as the acetylacetonate salt, is employed.

The results indicate that 98% of the hydroperoxide decomposes and quantitative analysis, by gas-liquid chromotography, of the resulting crude products shows a yield of phenol of 95% based on the hydroperoxide feed. The reaction product is a clear solution with no detectable quantities of any precipitate, indicating stability of the catatlyst.

EXAMPLE XV

The same procedure is followed in Example I, except that cyclohexylbenzene hydroperoxide and cyclohexane are employed as the hydroperoxide and diluent, respectively and a catalyst system comprised of 10 ppm of ruthenium and 50 ppm of chromium, each in the trivalent state and present as the acetylacetonate salt, is employed.

The results indicate that 99% of the hydroperoxide decomposes and quantitative analysis by gas-liquid chromotography, of the resulting crude products shows a yield of phenol and cyclohexanone of 89%, based on the hydroperoxide feed. The reaction product is a clear solution with no detectable quantities of any precipitate, indicating stability of the catalyst.

EXAMPLE XVI

The same procedure is followed as in Example I, except that cyclohexyl hydroperoxide and cyclohexane are employed as the hydroperoxide and diluent, respecitvely, and a catalyst system comprised of 20 ppm of ruthenium and 50 ppm of chromium, each in the trivaent state and present as the acetylacetonate salt, is employed.

The results indicate that 97% of the hydroperoxide decomposes and quantitative analysis, by gas-liquid chromotography, of the resulting crude products shows a yield of cyclohexanone and cyclohexanol of 84%, based on the hydroperoxide feed. The reaction product is a clear solution with no detectable quantities of any precipitate indicating stability of the catalyst.

We claim:

1. A process for the decomposition of a hydroperoxide comprising contacting the hydroperoxide with a catalytic quantity of a catalyst system comprising chromium and ruthenium while maintaining a hydroperoxide concentration during the reaction of at least 1 percent at a temperature of between about 25° C. and about 250° C. and a pressure sufficient to maintain the reactants in the liquid phase.

2. The process of claim 1 effected in continuous operation.

3. The process of claim 1 wherein the catalyst system is present in an amount of from about 0.01 ppm to 5000 ppm of ruthenium and of from about 0.01 ppm to 5000 ppm of chromium.

4. The process of claim 1 wherein the decomposition reaction is effected in the presence of a diluent.

5. The process of claim 1 wherein the ruthenium and chromium are present as compounds soluble in the reaction mixture.

6. The process of claim 5 wherein the hydroperoxide is of the formula:

$$R-OOH$$

wherein R is a member selected from the group consisting of hydrogen, a straight or branched chain alkyl group containing of from 2 to 15 carbon atoms, an aryl group, optionally substituted with one or more substituents inert to the decomposition reaction selected from the group consisting of alkyl or alkoxy of from 1 to 7 carbon atoms, nitro, carboxyl or carboxyl ester containing up to about 15 carbon atoms, halo-, or an alkaryl radical in which the alkyl chain contains of from 1 to 15 carbon atoms.

7. The process of claim 6 wherein the hydroperoxide is tertiary butyl hydroperoxide.

8. The process of claim 6 wherein the hydroperoxide is cyclohexyl hydroperoxide.

9. The process of claim 6 wherein the hydroperoxide is cumene hydroperoxide.

10. The process of claim 6 wherein the hydroperoxide is ethylbenzene hydroperoxide.

11. The process of claim 6 wherein the hydroperoxide is cyclohexylphenyl hydroperoxide.

12. The process of claim 5 wherein the ruthenuim and chromium catalyst is present in the form of at least one salt of a carboxylic acid.

13. The process of claim 5 wherein the catalyst comprises an admixture of ruthenium and chromium nitrates.

14. The process of claim 5 wherein the catalyst comprises an admixture of ruthenium and chromium sulfates.

15. The process of claim 3 wherein the diluent is a member selected from the group consisting of isobutane, tertiary butyl alcohol, ethyl benzene, cyclohexane and acetic acid.

16. The process of claim 1 wherein the decomposition reaction is effected at temperatures between about 25° C. and about 250° C. and a pressure of between about 0.1 and 150 atomospheres.

* * * * *